US009751958B2

(12) United States Patent
Funk et al.

(10) Patent No.: US 9,751,958 B2
(45) Date of Patent: Sep. 5, 2017

(54) USE OF HEATING STEAM CONDENSATE FOR PRODUCING WATER-ABSORBENT POLYMER PARTICLES

(75) Inventors: Rüdiger Funk, Niedernhausen (DE); Jürgen Schröder, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 729 days.

(21) Appl. No.: 13/498,364

(22) PCT Filed: Oct. 5, 2010

(86) PCT No.: PCT/EP2010/064776
§ 371 (c)(1),
(2), (4) Date: Mar. 27, 2012

(87) PCT Pub. No.: WO2011/042404
PCT Pub. Date: Apr. 14, 2011

(65) Prior Publication Data
US 2012/0202952 A1 Aug. 9, 2012

Related U.S. Application Data

(60) Provisional application No. 61/250,031, filed on Oct. 9, 2009.

(51) Int. Cl.
*A61L 15/22* (2006.01)
*A61L 15/24* (2006.01)
*A61L 15/60* (2006.01)
*C08F 2/18* (2006.01)
*C08F 2/00* (2006.01)
*C08F 220/06* (2006.01)
*C08F 222/10* (2006.01)

(52) U.S. Cl.
CPC ............ *C08F 2/18* (2013.01); *A61L 15/22* (2013.01); *C08F 2/00* (2013.01); *C08F 220/06* (2013.01); *C08F 222/1006* (2013.01)

(58) Field of Classification Search
CPC .... C08F 220/06; C08F 222/1006; C08F 2/00; C08F 2/18; A61L 15/22; A61L 15/24; A61L 15/60

USPC .......... 524/800, 804, 832, 845; 526/89, 207, 526/317.1; 523/326
See application file for complete search history.

(56) References Cited

U.S. PATENT DOCUMENTS

| 4,656,232 | A | 4/1987 | Nakaki et al. |
| 6,716,273 | B1 | 4/2004 | Schulte et al. |
| 6,987,151 | B2 * | 1/2006 | Gartner et al. ................ 526/65 |
| 8,119,755 | B2 | 2/2012 | Weismantel et al. |
| 2004/0110897 | A1 * | 6/2004 | Sakamoto et al. ............ 524/832 |
| 2005/0006219 | A1 | 1/2005 | Eck et al. |
| 2008/0004408 | A1 * | 1/2008 | Stueven et al. ................ 526/88 |
| 2008/0200623 | A1 | 8/2008 | Weismantel et al. |
| 2009/0023848 | A1 * | 1/2009 | Ahmed et al. ................ 524/422 |
| 2010/0016522 | A1 | 1/2010 | Stueven et al. |
| 2010/0056739 | A1 * | 3/2010 | Funk et al. ................ 526/317.1 |
| 2010/0197877 | A1 | 8/2010 | Funk et al. |

FOREIGN PATENT DOCUMENTS

| DE | 35 40 994 A1 | 5/1986 | |
| DE | 199 38 574 A1 | 2/2001 | |
| EP | 0 827 753 A2 | 3/1998 | |
| EP | 1 097 946 A2 | 5/2001 | |
| WO | WO-2005/007609 A1 | 1/2005 | |
| WO | WO-2007/028748 A1 | 3/2007 | |
| WO | WO-2008/037676 A1 | 4/2008 | |
| WO | WO 2008116840 A1 * | 10/2008 | ............ C07C 51/41 |
| WO | WO-2009/021921 A1 | 2/2009 | |

OTHER PUBLICATIONS

Data for Distilled water from Wikipedia; Jan. 12, 2007.*
Buchholz, Fredric L., et al. *Modern Superabsorbent Polymer Technology,* "Solution Polymerization: Unit Operations and Their Effect on Product Quality." New York: John Wiley & Sons, Inc., 1998, pp. 71-103.
International Search Report in International Application No. PCT/EP2010/064776, dated Jan. 11, 2011 (English translation).

* cited by examiner

*Primary Examiner* — Karuna P Reddy
(74) *Attorney, Agent, or Firm* — Marshall, Gerstein & Borun LLP

(57) ABSTRACT

The present invention relates to a process for producing water-absorbing polymer particles, wherein an aqueous monomer solution is polymerized and the monomer solution is prepared using steam condensate.

9 Claims, No Drawings

USE OF HEATING STEAM CONDENSATE FOR PRODUCING WATER-ABSORBENT POLYMER PARTICLES

CROSS-REFERENCE TO RELATED APPLICATIONS

This application is the U.S. national phase of International Application No. PCT/EP2010/064776, filed Oct. 5, 2010, which claims the benefit of U.S. provisional Application No. 61/250,031, filed Oct. 9, 2009, incorporated herein by reference in its entirety.

The present invention relates to a process for producing water-absorbing polymer particles, wherein an aqueous monomer solution is polymerized and the monomer solution is prepared using steam condensate.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The polymerization kinetics are unfavorably influenced by oxygen. It is therefore necessary to rule out the presence of oxygen in the polymerization. The monomer solutions used to produce water-absorbing polymer particles comprise dissolved oxygen. This oxygen is substantially removed before the polymerization. These processes are typically based on purging the monomer solution with nitrogen and removing the oxygen-enriched gas phase. In this so-called inertization, the nitrogen is usually conducted through the monomer solution in countercurrent. Good mixing of gas phase and monomer solution can be achieved, for example, by means of nozzles, static or dynamic mixers or bubble columns.

DE 35 40 994 A1 and EP 0 827 753 A2 disclose inertization in cocurrent, wherein the inert gas is sucked into the monomer solution to be inertized by means of a waterjet pump.

DE 199 38 574 A1 describes a typical bubble column, wherein the mixing of gas phase and monomer solution is improved by additional mixing tools.

EP 1 097 946 A2 proposes the use of ultrasound for improved removal of dispersed gas bubbles from the inertized monomer solution.

WO 2007/028748 A1 discloses a process for inertization, wherein a removal of the gas phase can be dispensed with.

It was an object of the present invention to provide an improved process for producing water-absorbing polymer particles; more particularly, the inertization of the monomer solution was to be optimized and the amount of inert gas needed lowered.

The object was achieved by a process for producing water-absorbing polymer particles by polymerizing a monomer solution or suspension comprising the preparation of an aqueous monomer solution or suspension by mixing
 a) at least one ethylenically unsaturated monomer bearing acid groups,
 b) optionally a neutralizing agent,
 c) water and
 d) at least one crosslinker,
inertizing the monomer solution, polymerizing the inertized monomer solution, optionally postneutralizing the resulting polymer gel, drying, grinding and classifying, wherein the water c) is at least partly steam condensate.

The present invention is based on the finding that steam condensate comprises virtually no dissolved oxygen. When aqueous monomer solutions or suspensions are prepared using steam condensate instead of demineralized water which has been customary to date, the proportion of dissolved oxygen in the aqueous monomer solution or suspension can already be lowered significantly before the inertization. This reduces the level of complexity needed to inertize the aqueous monomer solution or suspension.

The production of the water-absorbing polymer particles is explained in detail hereinafter:

The water-absorbing polymer particles are based on crosslinked polymers and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

The acid groups of the resulting polymer gels have typically been partially neutralized. Neutralization is preferably carried out at the monomer stage. This is typically done by mixing in the neutralizing agent b) as an aqueous solution or preferably also as a solid. The degree of neutralization is preferably from 25 to 85 mol %, for 'acidic' polymer gels more preferably from 30 to 60 mol %, most preferably from 35 to 55 mol %, for "neutral" polymer gels more preferably from 65 to 80 mol %, most preferably from 70 to 75 mol %, for which the customary neutralizing agents b) can be used, preferably alkali metal hydroxides, alkali metal oxides, alkali metal carbonates or alkali metal hydrogencarbonates and also mixtures thereof. Instead of alkali metal salts, it is also possible to use ammonium salts, such as the salt of triethanolamine. Particularly preferred alkali metals are sodium and potassium, but very particular preference is given to sodium hydroxide, sodium carbonate or sodium hydrogencarbonate and also mixtures thereof.

However, it is also possible to carry out at least some of neutralization after the polymerization, at the stage of the polymer gel formed in the polymerization (postneutralization). It is thus possible to neutralize up to 40 mol %, preferably 10 to 30 mol % and more preferably 15 to 25 mol % of the acid groups before the polymerization by adding a portion of the neutralizing agent b) actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

Water c) is used to adjust the water content of the monomer solution or suspension to the desired value, preferably of 40 to 75% by weight, more preferably of 45 to 70% by weight, most preferably of 50 to 65% by weight.

The water c) used is at least partly steam condensate. The proportion of steam condensate in the water c) is preferably at least 50% by weight, more preferably at least 90% by weight, most preferably at least 95% by weight.

Steam is typically raised by vaporizing specially prepared water, known as kettle feed water, under pressure, for example 1.5 bar, 4 bar, 16 bar or 100 bar, by means of suitable heat exchangers. For corrosion protection reasons, a reducing agent, for example hydrazine, is often added to the kettle feed water.

When the steam is condensed, the heat of vaporization is released again and can be used for heating purposes. The steam condensate obtained in the condensation is typically not used any further. The temperature at which the heat of vaporization is released here is a function of the steam pressure and is, for example, approx. 145° C. at 4 bar. By means of steam, for example, the air in the forced-air belt dryers used in the production of water-absorbing polymer particles is heated.

Steam condensate is virtually free of dissolved oxygen. A rise in the oxygen content should be avoided by excluding oxygen in the course of storage and transport of the steam condensate.

The steam condensate comprises preferably less than 1 ppm, more preferably less than 0.5 ppm, most preferably less than 0.1 ppm, of dissolved oxygen. The oxygen content is measured by means of commercial oxygen probes at 20° C. and atmospheric pressure.

Suitable crosslinkers d) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers d).

Crosslinkers d) are preferably compounds having at least two polymerizable groups which can be polymerized free-radically into the polymer network. Suitable crosslinkers d) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers d) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers d) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker d) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The monomer solution or suspension is inertized, typically using nitrogen as the inert gas, such that the oxygen content of the inertized monomer solution or suspension is preferably less than 1 ppm, more preferably less than 0.5 ppm, most preferably less than 0.1 ppm.

Typically, initiators are added to the monomer solution or suspension after the inertization.

The initiators used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

The monomer solution or suspension may further comprise ethylenically unsaturated monomers copolymerizable with the ethylenically unsaturated monomers a) bearing acid groups. Such monomers are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

In addition, the monomer solution or suspension may also comprise water-soluble polymers, for example polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (fines) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of EDANA (European Disposables and Nonwovens Association) recommended test method No. WSP 220.2-05 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization. When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 98% by weight.

The proportion of particles having a particle size of at most 600 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles may be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

Polyvalent cations may be applied to the particle surface in addition to the surface postcrosslinkers before, during or after the surface postcrosslinking.

The usable polyvalent cations are, for example, divalent cations such as the cations of zinc, magnesium, calcium and strontium, trivalent cations such as the cations of aluminum, tetravalent cations such as the cations of titanium and zirconium. Possible counterions are, for example, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying. The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is carried out preferably at 30 to 80° C., more preferably at 35 to 70° C. and most preferably at 40 to 60° C. At excessively low temperatures, the water-absorbing polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles have a moisture content of preferably 1 to 15% by weight, more preferably 2 to 10% by weight, most preferably 3 to 5% by weight, the water content being determined by EDANA (European Disposables and Nonwovens Association) recommended test method No. WSP 230.2-05 "Moisture Content".

The water-absorbing polymer particles have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA (European Disposables and Nonwovens Association) recommended test method No. WSP 241.2-05 "Centrifuge Retention Capacity".

The water-absorbing polymer particles have an absorption under a pressure of 49.2 g/cm² of typically at least 15 g/g, preferably at least 20 g/g, preferentially at least 22 g/g, more preferably at least 24 g/g, most preferably at least 26 g/g. The absorption under a pressure of 49.2 g/cm² of the water-absorbing polymer particles is typically less than 35 g/g. The absorption under a pressure of 49.2 g/cm² is determined analogously to EDANA (European Disposables and Nonwovens Association) recommended test method No. WSP 242.2-05 "Absorption under Pressure", except that a pressure of 49.2 g/cm² is established instead of a pressure of 21.0 g/cm².

Example

In a plant for producing water-absorbing polymer particles, the air used in a forced-air belt dryer was heated by means of steam. The oxygen content of the steam condensate obtained was measured and was less than 0.1 ppm, i.e. the steam condensate did not comprise any detectable amounts of dissolved oxygen.

For comparison, the oxygen content of the demineralized water available in the plant was measured. The demineralized water comprised 8 ppm of dissolved oxygen.

The invention claimed is:

1. A process for producing water-absorbing polymer particles, comprising preparing an aqueous monomer solution or suspension by mixing
   a) at least one ethylenically unsaturated monomer bearing an acid group,
   b) optionally a neutralizing agent,
   c) water at least partly as a steam condensate and the steam condensate comprises less than 1 ppm of dissolved oxygen, and
   d) at least one crosslinker,
then inertizing the monomer solution or suspension, polymerizing the inertized monomer solution or suspension, then drying the resulting polymer gel, grinding, and classifying, wherein the steam condensate is obtained from the condensation of steam in heat exchangers used for drying air in forced air belt dryers in the drying step.

2. The process according to claim 1, wherein the water c) is steam condensate to an extent of at least 50% by weight.

3. The process according to claim 1, wherein the oxygen content of the aqueous monomer solution or suspension is lowered below 1 ppm by inertization.

4. The process according to claim 1, wherein the monomer a) is acrylic acid partly neutralized to an extent of at least 50 mol %.

5. The process according to claim 1, wherein the monomer a) has been neutralized to an extent of 25 to 85 mol %.

6. The process according to claim 1, wherein the steam condensate comprises less than 0.5 ppm of dissolved oxygen.

7. The process according to claim 1, wherein the steam condensate comprises less than 0.1 ppm of dissolved oxygen.

8. The process according to claim 1, wherein the water c) is steam condensate to an extent of at least 90% by weight.

9. The process according to claim 1, wherein the water c) is steam condensate to an extent of at least 95% by weight.

* * * * *